(12) United States Patent
Clifford et al.

(10) Patent No.: US 11,612,526 B2
(45) Date of Patent: Mar. 28, 2023

(54) INSERT PATCH WITH LIQUID BARRIER

(71) Applicant: PRINCIPLE BUSINESS ENTERPRISES, INC., Dunbridge, OH (US)

(72) Inventors: Alan Clifford, Marion, OH (US); Joel Geerken, Waterville, OH (US)

(73) Assignee: PRINCIPLE BUSINESS ENTERPRISES, INC., Dunbridge, OH (US)

( * ) Notice: Subject to any disclaimer, the term of this patent is extended or adjusted under 35 U.S.C. 154(b) by 1044 days.

(21) Appl. No.: 16/357,559

(22) Filed: Mar. 19, 2019

(65) Prior Publication Data
US 2019/0290509 A1 Sep. 26, 2019

Related U.S. Application Data

(60) Provisional application No. 62/647,192, filed on Mar. 23, 2018.

(51) Int. Cl.
| | | |
|---|---|---|
| *A61F 13/494* | (2006.01) | |
| *A61F 13/76* | (2006.01) | |
| *A61F 13/539* | (2006.01) | |
| *A61F 13/62* | (2006.01) | |
| *A61F 13/49* | (2006.01) | |

(52) U.S. Cl.
CPC ........ *A61F 13/76* (2013.01); *A61F 13/49466* (2013.01); *A61F 13/539* (2013.01); *A61F 13/62* (2013.01); *A61F 2013/49092* (2013.01); *A61F 2013/53908* (2013.01)

(58) Field of Classification Search
CPC .. A61F 13/49466; A61F 13/539; A61F 13/76; A61F 2013/49092; A61F 2013/49493
See application file for complete search history.

(56) References Cited

U.S. PATENT DOCUMENTS

| | | | |
|---|---|---|---|
| 5,069,672 A | | 12/1991 | Wippler et al. |
| 5,360,422 A | | 11/1994 | Brownlee et al. |
| 5,531,730 A | * | 7/1996 | Dreier ............... A61F 13/49406 604/385.19 |
| 5,938,652 A | * | 8/1999 | Sauer .................... A61F 13/495 604/386 |
| 5,993,433 A | | 11/1999 | St. Louis et al. |

(Continued)

*Primary Examiner* — Catharine L Anderson
(74) *Attorney, Agent, or Firm* — Ward Law Office LLC; Jacob M. Ward

(57) ABSTRACT

A disposable absorbent underwear product includes a garment layer, an absorbent insert, a non-woven patch, and a barrier. The absorbent insert has a fluid-impermeable base layer, an absorbent core, and a fluid-permeable top layer. The non-woven patch covers an end of the absorbent insert. A first portion of the non-woven patch is adhered to both the fluid-permeable top layer of the absorbent insert and the garment layer with an adhesive. A second portion of the non-woven patch is free and forms a pouch. An end portion of the absorbent core is disposed adjacent to the second portion of the non-woven patch. The barrier extends along a width of the absorbent insert. The barrier extends through the fluid-permeable top layer of the absorbent core and connects the fluid-impermeable base layer and the one non-woven patch to direct fluid flow to the absorbent core and militate against fluid overflow.

16 Claims, 5 Drawing Sheets

(56) References Cited

U.S. PATENT DOCUMENTS

| | | | | |
|---|---|---|---|---|
| 6,132,410 | A | * | 10/2000 | Van Gompel ..... A61F 13/49466 604/385.25 |
| 6,217,563 | B1 | * | 4/2001 | Van Gompel ..... A61F 13/49466 604/385.101 |
| 6,264,641 | B1 | * | 7/2001 | Van Gompel ..... A61F 13/53708 604/385.01 |
| 7,166,095 | B1 | | 1/2007 | Coates |
| 9,044,358 | B2 | * | 6/2015 | Nakajima ......... A61F 13/49466 |
| 9,308,131 | B2 | | 4/2016 | Evenson et al. |
| 2017/0246054 | A1 | * | 8/2017 | Bishop ................. A61F 13/494 |

* cited by examiner

INSERT PATCH WITH LIQUID BARRIER

CROSS REFERENCE TO RELATED APPLICATIONS

This application claims the benefit of U.S. Provisional Application Ser. No. 62/647,192, filed on Mar. 23, 2018. The entire disclosure of the above application is hereby incorporated herein by reference.

FIELD

The present disclosure relates to absorbent products and, more particularly, to a disposable absorbent underwear product.

BACKGROUND

Incontinence is a condition from which a great many individuals suffer. The inability to restrain or control the discharge of bodily waste, such as urine and feces, is a problem that often cannot be remedied.

Consequently, it is necessary to provide the incontinent individual with means for containing such discharges. Especially for adults with incontinence, adult diapers or disposable absorbent underwear products, sometimes referred to as "DAU," are used for this purpose.

Known disposable absorbent underwear products have a moisture absorbent insert containing a core with absorbent materials such as wood pulp, tissue wadding, foams, non-woven, batting, or the like. The core is typically covered on one side by a liquid permeable cover sheet, and on another side by a liquid impermeable back sheet, which together contain and maintain the integrity of, and define, the moisture absorbent insert.

For example, U.S. Pat. No. 5,069,672 to Wippler et al. teaches a reusable diaper having substantially rectangular inner and outer layers of absorbent material, a liquid impervious layer between the inner and outer layers, and first and second pockets on the inner layer, and wherein the open sides of the first and second pockets are oriented toward each other. In another example, U.S. Pat. No. 9,308,131 to Evenson et al. teaches disposable absorbent garments or containment pants that include a fluid-impervious base sheet and a containment flap joined with the base sheet to create a fluid-impervious pouch.

Nonetheless, these known diapers and disposable absorbent underwear have been found insufficient for addressing fluid overflowing from the absorbent core during urination. In particular, males are known to urinate toward the front of the insert, rather than directly onto the absorbent core, which often results in such overflow situations.

There is a continuing need for a disposable absorbent underwear product that militates against an overflow of excess fluid. Desirably, the absorbent underwear product is configured that redirect the excess fluid to the absorbent core of the product.

SUMMARY

In concordance with the instant disclosure, a disposable absorbent underwear product that militates against an overflow of excess fluid, and which is configured to redirect the excess fluid to the absorbent core of the product, has been surprisingly discovered.

In one embodiment, a disposable absorbent underwear product has a garment layer and an absorbent insert. The absorbent insert is disposed on the garment layer. The absorbent insert has a top layer that is fluid-permeable, an absorbent core, and a base layer that is fluid-impermeable. The absorbent core has a first end and a second end. The base layer also has a first terminal end and a second terminal end. The first end of the absorbent core is spaced apart from the first terminal end of the base layer. There is also a non-woven patch disposed on and covering the first terminal end of the base layer of the absorbent insert. The non-woven patch has a first portion and a second portion. The first portion of the non-woven patch is adhered to both the top layer of the absorbent insert and the garment layer. The second portion of the non-woven patch is bounded by the first portion and is unadhered to the top layer of the absorbent insert. The second portion of the non-woven patch together with the top layer of the absorbent insert define a pouch with an opening for receiving excess fluid. A barrier or dam is disposed through each of the first portion of the non-woven patch and the top layer of the absorbent insert. The barrier connects first portion of the non-woven patch and the base layer of the absorbent insert. The barrier is also disposed between the first end of the absorbent core and the first terminal end of the base layer of the absorbent insert. The barrier also directs fluid flow to the absorbent core and militate against fluid overflow onto the garment layer.

In another embodiment, the base layer has a base layer width, the barrier has a barrier length, and the non-woven patch has a patch width. The barrier length is greater than the base layer width, and the barrier is adhered to the garment layer on opposing sides of the base layer. The barrier is also disposed across an entirety of the base layer width. The barrier length is also less than the patch width. Further, the first portion of the non-woven patch is substantially U-shaped with a pair of arm sections. The second portion of the non-woven patch is disposed between and bounded by the arm sections. The first and second portions together with the top layer of the absorbent insert define the open pouch of the product.

In a further embodiment, a disposable absorbent underwear product includes a garment layer, an absorbent insert, a first non-woven patch, a first barrier, a second non-woven patch, and a second barrier. The absorbent insert is disposed on the garment layer. The absorbent insert has a top layer that is fluid-permeable, an absorbent core, and a base layer that is fluid-impermeable. The absorbent core has a first end and a second end. The base layer has a first terminal end and a second terminal end. The first end of the absorbent core is spaced apart from the first terminal end of the base layer. The first non-woven patch is disposed on and covers the first terminal end of the base layer of the absorbent insert. The first non-woven patch has a first portion and a second portion. The first portion of the first non-woven patch is adhered to both the top layer of the absorbent insert and the garment layer. The second portion of the first non-woven patch is bounded by the first portion and is unadhered to the top layer of the absorbent insert. The second portion of the first non-woven patch together with the top layer of the absorbent insert define a first pouch with a first opening for receiving excess fluid. The first barrier is disposed through each of the first portion of the first non-woven patch and the top layer of the absorbent insert and connected to the base layer of the absorbent insert. The first barrier is also disposed between the first end of the absorbent core and the first terminal end of the base layer of the absorbent insert. The first barrier is also configured to direct fluid flow to the absorbent core and militate against fluid overflow. The second non-woven patch is disposed on and covers the second terminal end of the base layer of the absorbent insert. The second non-woven patch has a first portion and a second portion. The first portion of the second non-woven patch is adhered to both the top layer of the absorbent insert and the garment layer. The second portion of the second non-woven patch is bounded by the first portion and together with the top layer of the absorbent insert defines a second pouch with a second opening for receiving the excess fluid. The second barrier is disposed through each of the first portion of the second non-woven patch and the top layer of the absorbent insert. The second barrier is connected to the base layer of the absorbent insert. The second barrier is disposed between the second end of the absorbent core and the second terminal end of the base layer of the absorbent insert, and is also configured to direct fluid flow to the absorbent core and militate against fluid overflow to the garment layer. The second opening of the second pouch of the second non-woven patch faces the first opening of the first pouch of the first non-woven patch.

In an exemplary embodiment, a disposable absorbent underwear product has an insert with a polypropylene base layer, a porous non-woven top layer, and an absorbent core sandwiched therebetween. The insert is generally attached to a garment layer with an adhesive. The ends of the insert and the interior absorbent core are covered by patches, one of which is located at each end of the insert. Importantly, the insert does not extend to the ends of the belly band section of the garment layer, which thereby minimizes the amount of insert material used in the product. Each patch is also attached on three sides to the garment layer by an adhesive, and is open with a free side facing a center of the insert and garment layer. The patch is also attached to the polypropylene base of the insert by an adhesive barrier that penetrates the nonwoven top layer of the insert. The barrier extends along a width of the insert, and together with the patch directs any overflow of fluids back to the absorbent core. The disposable absorbent underwear product may also contain standing leg cuffs, which will end under the patch and be glued down to the insert at the ends.

DRAWINGS

The above, as well as other advantages of the present disclosure, will become readily apparent to those skilled in the art from the following detailed description, particularly when considered in the light of the drawings described hereafter.

Figure 2:
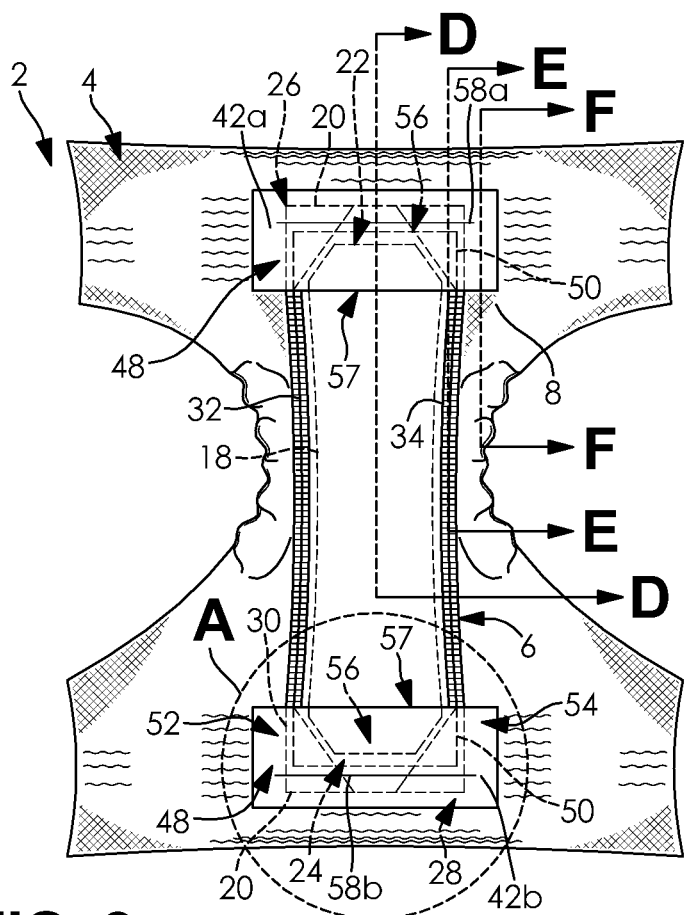
FIG. 2 is a top plan view of the disposable absorbent underwear product shown in FIG. 1, and the disposable absorbent underwear product illustrated with the patch on each side of the absorbent insert.
Figure 8:
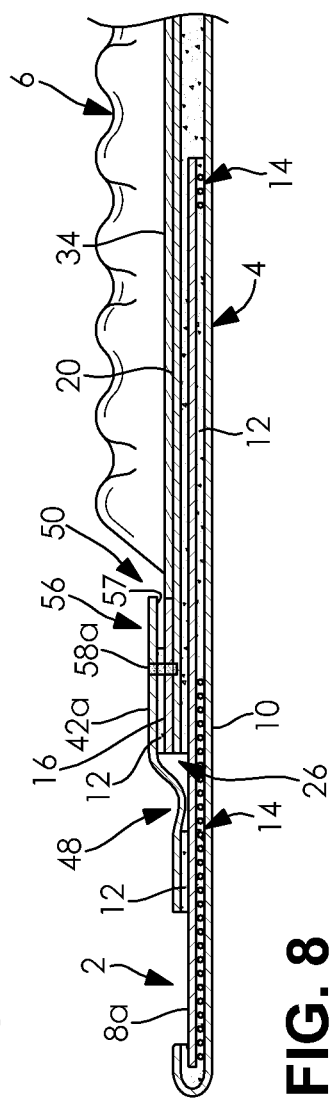
Figure 9:
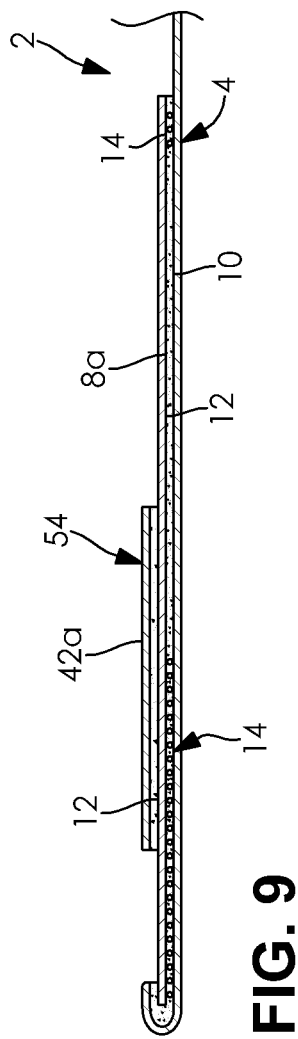

FIG. 8 is a fragmentary, cross-sectional, right side elevational view of the disposable absorbent underwear product taken at section line E-E in FIG. 2, and showing the patch, the top layer, the base layer, the second leg cuff, the barrier, and the garment layer at a location laterally offset from the center line of the disposable absorbent underwear product; and FIG. 9 is a fragmentary, cross-sectional, right side elevational view of the disposable absorbent underwear product taken at section line F-F in FIG. 2, and showing the patch adhered to the garment layer.

DETAILED DESCRIPTION

The following description is merely exemplary in nature and is not intended to limit the present disclosure, application, or uses. It should also be understood that throughout the drawings, corresponding reference numerals indicate like or corresponding parts and features.

FIGS. 1-9 illustrate a disposable absorbent underwear product 2 according to various embodiment of the disclosure. The disposable absorbent underwear product 2 has a garment layer 4 with an absorbent insert 6 disposed thereon. While described and shown in the drawings herein primarily with reference to an absorbent adult pant product, it should be appreciated that the disposable absorbent underwear product 2 may be any absorbent product configured to be worn by an individual user, including children and adults, such as absorbent underwear, reusable diapers, or disposable diapers, as desired.

Figure 1:
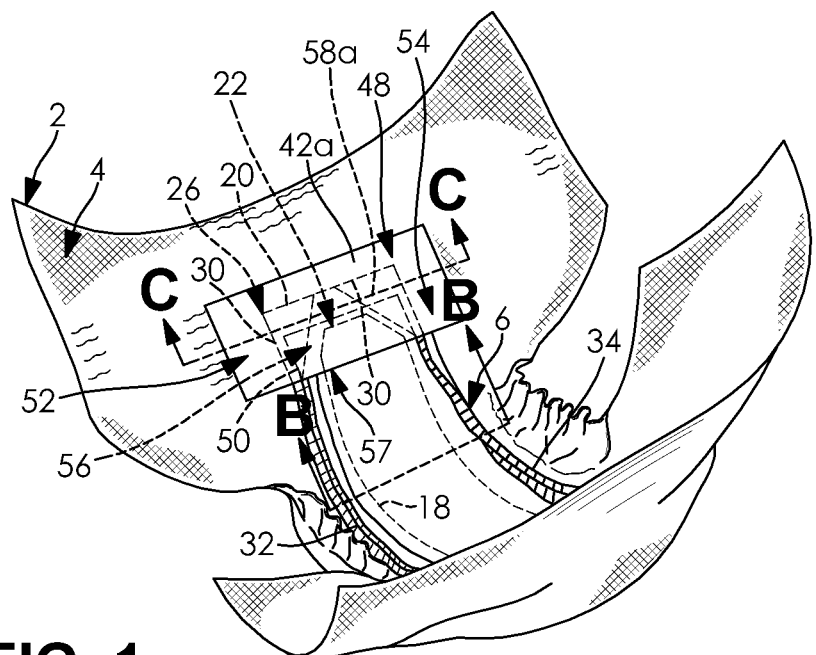
FIG. 1 is a top perspective view of a disposable absorbent underwear product according to one embodiment of the present disclosure, and the disposable absorbent underwear product shown having a barrier, a patch, an absorbent insert, and a garment layer.
Figure 3:
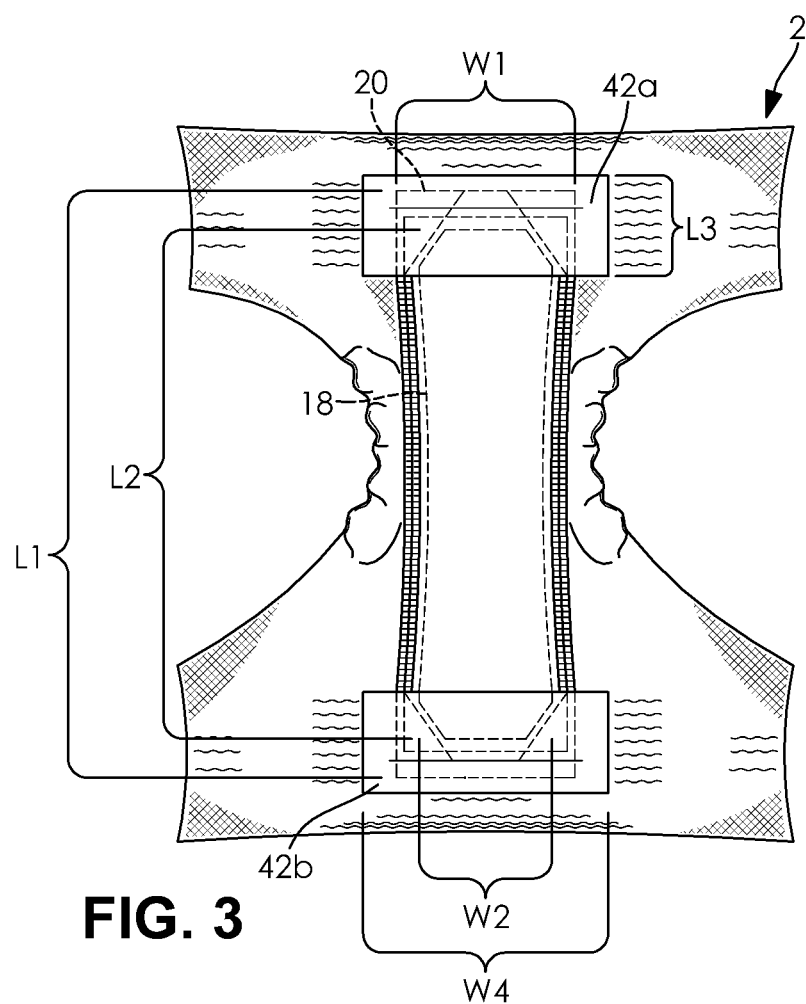
FIG. 3 is another top plan view of the disposable absorbent underwear product shown in FIG. 1, and the disposable absorbent underwear product illustrated with the patch on each side of the insert and depicting relative dimensions of the patch, the absorbent core of the insert, and the base layer of the insert.

With reference to FIGS. 1-3, the garment layer 4 may by substantially hour-glass shaped in certain embodiments. The hour-glass shape may facilitate a wearing of the disposable absorbent underwear product 2 by the user. Advantageously, a middle portion of the disposable absorbent underwear product 2 may be narrower than an outer portion of the disposable absorbent underwear product 2. The middle portion is adapted to support a groin of the user, while the outer portion is configured to be secured to a waist of the user. However, it should be appreciated that any shape of the disposable absorbent underwear product 2 may be chosen by one skilled in the art within the scope of the present disclosure.

Figure 5:
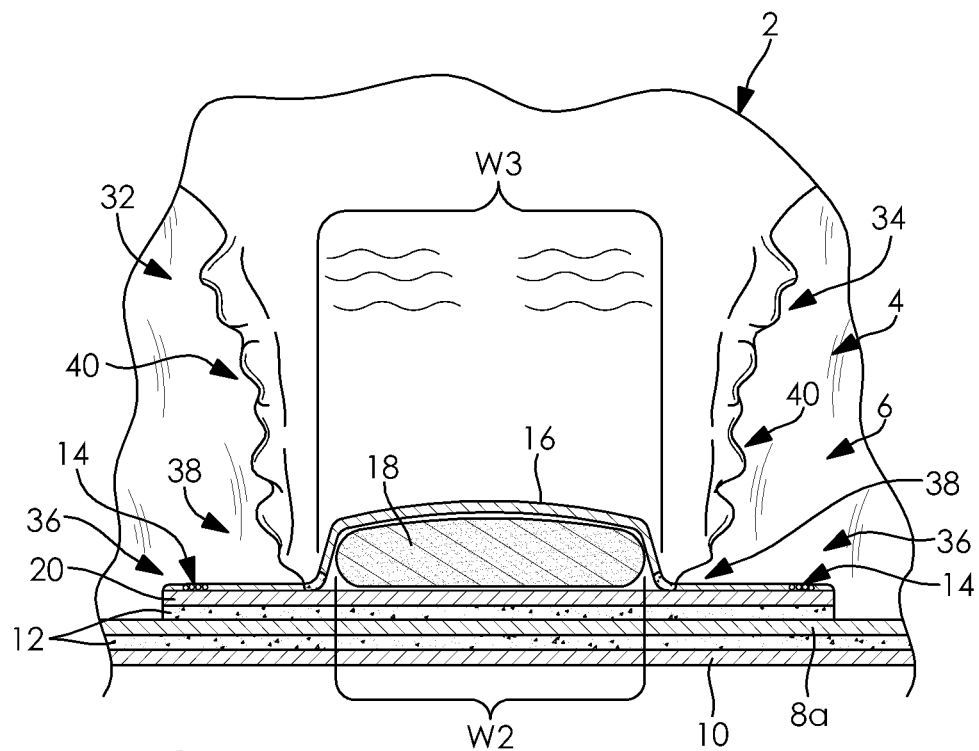
FIG. 5 is an enlarged, fragmentary, cross-sectional, front elevational view of the insert and the garment layer taken at section line B-B in FIG. 1, and showing a first leg cuff and a second leg cuff bound to a top layer and a base layer of the insert.
Figure 6:
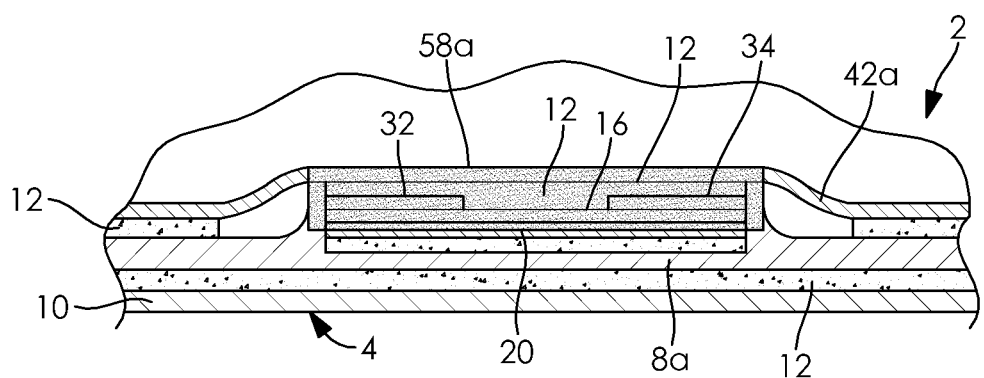
FIG. 6 is an enlarged, fragmentary, cross-sectional, front elevational view taken at section line C-C in FIG. 1, and illustrating the barrier being disposed through the non-woven patch, the top layer of the insert, the leg cuffs, and a portion of the base layer.
Figure 7:
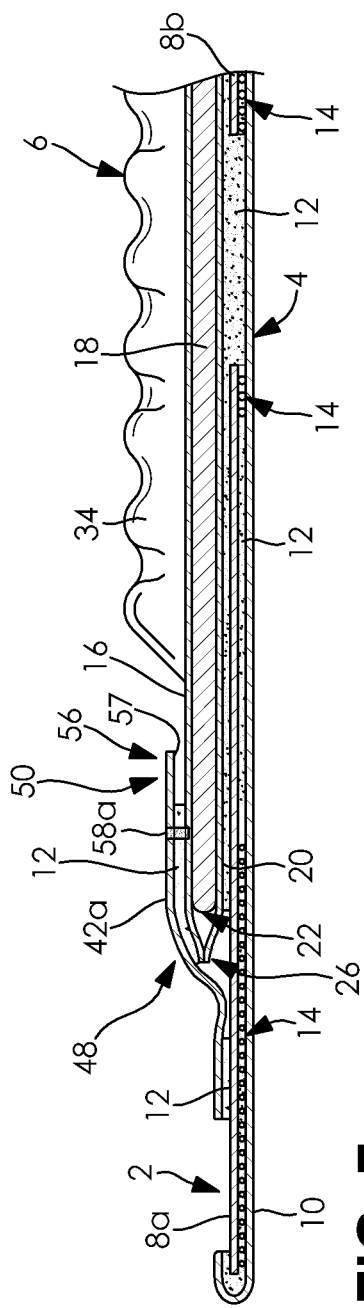
FIG. 7 is a fragmentary, cross-sectional, right side elevational view of the disposable absorbent underwear product taken at section line D-D in FIG. 2, and showing the patch, the top layer, the absorbent core, the base layer, the second leg cuff, the barrier, and the garment layer at a center line of the disposable absorbent underwear product.

In particular embodiments, as shown in FIGS. 2 and 5-9, the garment layer 4 may include an inner garment layer 8, 8a, 8b and an outer garment layer 10. The inner garment layer 8, 8a, 8b may include a first inner garment layer 8a and a second inner garment layer 8b. The first inner garment layer 8a may be spaced apart from the second inner garment layer 8b, as shown in FIG. 7. For example, the first inner garment layer 8a and the second inner garment layer 8b may be secured to the outer garment layer 10 by an adhesive 12 such as a construction hotmelt adhesive. Other suitable means for securing the inner garment layer 8a, 8b to the outer garment layer 10 may also be employed, as desired.

As non-limiting examples, the inner garment layer 8a, 8b and the outer garment layer 10 may each be formed from a non-woven material, such as polyester, polyolefin, rayon, or of natural fibers such as cotton. The fibers of the non-woven material are typically bound together by a thermal binding procedure or by a polymeric binder such as polyacrylate. In a particular example, the inner garment layer 8 may be manufactured using a spunbond/meltblown/spunbond (SMS) phobic non-woven material, and the outer garment layer 10 may be manufactured using polypropylene spunbond (SBPP) phobic non-woven material. However, it should be appreciated that a skilled artisan may select any other suitable material for the inner garment layer 8a, 8b and the outer garment layer 10 within the scope of the disclosure.

With reference to FIGS. 7-9, a plurality of elastic fibers 14 may be disposed between the inner garment layer 8 and the outer garment layer 10. The elastic fibers 14 permit a belly band area of the diaper to stretch and flex, allowing the user to secure the disposable absorbent underwear product 2 around their waist. In particular embodiments, the elastic fibers 14 may be covered in the adhesive 12, and thereby serve to further bind the inner garment layer 8a, 8b and the outer garment layer 10. To militate against undesired disconnection of the outer garment layer 10 from the inner garment layer 8a, 8b, a free end of the outer garment layer 10 may also be folded over and adhered to the inner garment layer 8a, 8b, as shown in FIGS. 7-9. It should be appreciated that the free end of the outer garment layer 10 may be adhered to the inner garment layer 8 on any portion of an outer perimeter of the disposable absorbent underwear product 2, as desired.

Figure 4:
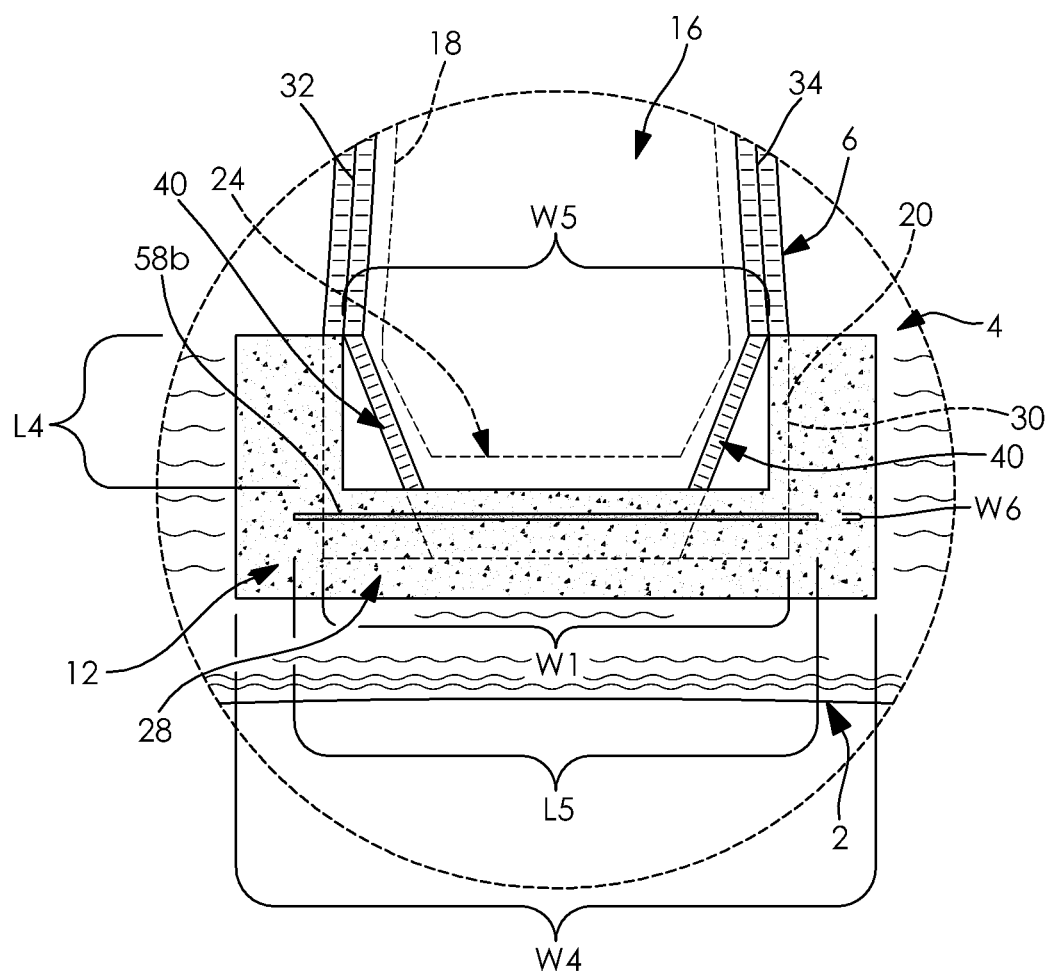
FIG. 4 is an enlarged, fragmentary, top plan view taken at call-out A in FIG. 2, and showing the adhesive layer disposed beneath the patch and the barrier being wider than the base layer, and further illustrating relative dimensions of a portion of the patch and the barrier.

With renewed reference to FIGS. 1-9, the absorbent insert 6 may be attached to the garment layer 4 of the disposable absorbent underwear product 2. In a particular embodiment, as shown in FIG. 5, the absorbent insert 6 includes a top layer 16, an absorbent core 18, and a base layer 20. The absorbent core 18 is disposed between and encapsulated by the top layer 16 and the base layer 20. For example, the top layer 16 may be superposed over a first face of an absorbent core 18, and the base layer 20 may be superposed over a second face of the absorbent core 18, with the second face being disposed opposite the first face. In certain embodiments, an acquisition layer (not shown) may be disposed between the absorbent core 18 and the top layer 16 of the insert 6. It should be appreciated that the acquisition layer may facilitate a distribution of fluid to the absorbent core 18.

It should be appreciated that the top layer 16 may be substantially porous and adapted to permit fluid pass therethrough into the underlying absorbent core 18. In certain embodiments, the top layer 16 may be a porous, non-woven, hydrophobic material. The non-woven material may be manufactured in part or completely of synthetic fibers or films, including such materials as polyester, polyolefin, rayon, or the like, or of natural fibers such as cotton. The fibers of the non-woven material are typically bound together by a thermal binding procedure or by a polymeric binder such as polyacrylate. A skilled artisan may also select other suitable porous materials for the top layer 16, as desired.

The base layer 20 is fluid-tight or liquid impervious. In particular, the base layer 20 may be a thin, substantially liquid impermeable web or sheet of plastic film such as polyethylene, polypropylene, polyvinyl chloride or similar material. The base layer 20 may further be formed of a compostable material such as a web or sheet of polyvinyl alcohol-based film. One of ordinary skill in the art may also select other suitable liquid impervious materials for the base layer 20 within the scope of the disclosure.

The absorbent core 18 is comprised of hydrophilic or superabsorbent materials.

For example, the absorbent core 18 may include a web or batt of hydrophilic or superabsorbent material in one or more distinct zones or layers. In further examples, the absorbent core 18 may be a synthetic high-absorbency material including the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core 18 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present disclosure. A skilled artisan may also select other suitable highly absorbent materials for the absorbent core 18, as desired.

As shown in FIGS. 5-9, the absorbent insert 6 is generally adhered to the garment layer 4 on an interior of the disposable absorbent underwear product 2 with the adhesive 12. As a non-limiting example, the adhesive 12 may be a construction glue or hotmelt, but it should be appreciated that other suitable adhesives may be employed. In particular, as shown in FIGS. 5 and 7, the base layer 20 of the insert 6 may be adhered to the first inner garment layer 8a, the second inner garment layer 8b, and the outer garment layer 10 with the adhesive 12. As also shown in FIG. 7, the base layer 20 may also be adhered to the outer garment layer 10 at an area disposed between the first inner garment layer 8a and the second inner garment layer 8b.

With reference to FIGS. 1-2, 4, and 7, the absorbent core 18 may have a first end 22 and a second end 24. Also, the base layer 20 may have a first terminal end 26 and a second terminal end 28. The first terminal end 26 and the second terminal end 28 of the base layer 20 may also serve as the first and second terminal ends 26, 28 of the absorbent insert 6 as a whole. In particular examples, the base layer 20 may be longer than the absorbent core 18, such that the first end 22 of the absorbent core 18 may be spaced apart from the first terminal end 26 of the base layer 20, and the second end 24 of the absorbent core 18 may be spaced apart from the second terminal end 28 of the base layer 20. The spacing apart of the first and second ends 22, 24 of the absorbent core 18 from the first and second terminal ends 26, 28 of the base layer 20, respectively, may thereby ensure that the absorbent core 18 is disposed within a perimeter 30 of the base layer 20.

With reference to FIG. 3, the base layer 20 may have a minimum width W1 that is greater than a maximum width W2 of the absorbent core 18. As shown in FIG. 5, the top layer 16 may also have a minimum width W3 that is greater than the maximum width W2 of the absorbent core 18. It should be appreciated that the top layer 16 and the base layer 20 being wider than the absorbent core 18 provides for side or marginal portions of the base layer 20 and top layer 16, which extend past an outermost perimeter of the absorbent core 18. In certain embodiments, the base layer 20 and the top layer 16 may be adhered or otherwise fused together in these side or marginal portions to encapsulate the absorbent core 18. For example, the top layer 16 and the base layer 20 may be secured to one another by the adhesive 12, a thermo-embossing process, or any other suitable method chosen by one skilled in the art.

In certain embodiments, each of the top layer 16 and the base layer 20 may have substantially a same length L1. Furthermore, with reference to FIG. 3, a length L1 of each of the top layer 16 and the base layer 20 may also be greater than a length L2 of the absorbent core 18. The relatively greater length L1 of the top and base layers 16, 20, together with the relatively greater widths W1, W3 of the top and base layers 16, 20, renders the absorbent core 18 disposed entirely within both the outermost perimeter of the top layer 16 and the perimeter 30 of the base layer 20. It should be appreciated that the absorbent core 18 being disposed within the perimeter 30 of the otherwise fluid-impermeable base layer 20 militates against undesirable liquid overflow from the absorbent core 18 onto the surrounding garment layer 4 in operation.

As one example, and as shown in FIG. 3, the width W1 of the base layer 20 may be between about one hundred and ninety millimeters (190 mm) and about two hundred and fifty millimeters (250 mm), and most particularly, may be about two hundred and twenty millimeters (220 mm). The length L1 of the base layer 20 may be between about five hundred and forty millimeters (540 mm) and six hundred millimeters (600 mm) and, most particularly, may be about five hundred and seventy millimeters (570 mm).

In another non-limiting example, also shown in FIG. 3, the maximum width W2 of the absorbent core 18 may be between about one hundred and fifty millimeters (150 mm) and about one hundred and ninety millimeters (190 mm), and most particularly, may be about one hundred and seventy millimeters (170 mm). The length L2 of the absorbent core 18 may be between about four hundred and sixty millimeters (460 mm) and about five hundred and twenty millimeters (520 mm), and most particularly, may be about four hundred and ninety millimeters (490 mm).

In a further example, and as shown in FIG. 5, the width W3 of the top layer 16 may be between about one hundred and forty-five millimeters (145 mm) and about one hundred and eighty-five millimeters (185 mm), and most particularly, may be one hundred and sixty-five millimeters (165 mm). As shown in FIG. 3, the length L1 of the top layer 16 may be between about five hundred and forty millimeters (540 mm) and about six hundred millimeters (600 mm), and most particularly, may be about five hundred and seventy millimeters (570 mm).

It should be appreciated that the above-mentioned specific widths W1, W2, and W3 and lengths L1, L2 are being provided for illustration purposes only, with respect to a particular absorbent adult pant product 2 of the present disclosure, and are otherwise non-limiting. Although each of the top layer 16 and the base layer 20 are described as having the same length L1, embodiment in which the top layer 16 and the base layer 20 have different lengths are also contemplated and considered within the scope of the disclosure. It should further be appreciated that one skilled in the art may select any other dimensions W1, W2, W3, L1, L2 for the top layer 16, the absorbent core 18, and the base layer 20, respectively, as desired.

In particular embodiments, with reference to FIGS. 1-8, the insert 6 may also have a pair of leg cuffs 32, 34, which may include a first leg cuff 32 and second leg cuff 34. The second leg cuff 34 may be on an opposite side of the absorbent core 18 relative to the first leg cuff 32. As shown in FIG. 5, each of the leg cuffs 32, 34 may have a pair of bottom portions 36, a middle portion 38, and a pair of top portions 40. In specific embodiments, the bottom portions 36 of each of the leg cuffs 32, 34 may be adhered to the base layer 20, and the middle portion 38 of each of the leg cuffs 32, 34 may be adhered to both the top layer 16 and the base layer 20 of the absorbent insert 6. It should be understood that the middle portion 38 of each of the leg cuffs 32, 34 being adhered to each of the top layer 16 and base layer 20 of the insert 6 serves to laterally secure the absorbent core 18 between the first leg cuff 32 and the second leg cuff 34.

Furthermore, the top portions 40 of each of the leg cuffs 32, 34 may be adhered to the top layer 16 of the insert 6 at location adjacent the first end 22 and the second end 24 of the absorbent core 18, respectively. For example, as shown in FIG. 4, the top portions 40 of each of the leg cuffs 32, 34 may be secured at an angle relative to the top layer 16 of the insert 6 adjacent the first and second ends 22, 24 of the absorbent core 18. It should be appreciated that the adhering of the top portions 40 of each of the leg cuff 32, 34 to the top layer 16 at the locations adjacent the ends 22, 24 of the absorbent core 18 may secure each leg cuff 32, 34 in an orientation that mitigates an undesirable overflow of fluids on either side of the absorbent core 18.

The materials forming the leg cuffs 32, 34 may be the same as or different from the materials forming the garment layer 4. As a non-limiting example, each of the leg cuffs 32, 34 may be formed from non-woven material and the elastic 14, for example, as shown in FIG. 5. The non-woven material may be manufactured in part or completely of synthetic fibers or films, including such materials as polyester, polyolefin, rayon, or the like, or of natural fibers such as cotton. The fibers of the non-woven material are typically bound together by a thermal binding procedure or by a polymeric binder. In a specific example, each of the leg cuffs 32, 34 may be an SBPP zone treated non-woven material. However, it should be appreciated that each of the leg cuffs 32, 34 may be manufactured using any other suitable material, as desired.

Advantageously, and with renewed reference to FIGS. 1-3 and 7-8, each of the first and second terminal ends 26, 28 of the absorbent insert 6 may be covered by a first and second patch 42a, 42b, respectively. Although described herein with respect to two patches 42a, 42b, it should be appreciated that embodiments having a single patch 42a, 42b are contemplated and considered within the scope of the present disclosure. The first and second patch 42a, 42b are configured to militate against overflow of fluid from the absorbent insert 6 as described further herein.

In particular embodiments, as shown in FIGS. 2 and 3, the first patch 42a may cover both the first terminal end 26 of the base layer 20 and the first end 22 of the absorbent core 18, and the second patch 42b may cover both the second terminal end 28 of the base layer 20 and the second end 24 of the absorbent core 18.

Moreover, each of the first and second patches 42a, 42b may be manufactured of a hydrophobic non-woven material. The non-woven material may be made in part or completely of synthetic fibers or films of materials such as polyester, polyolefin, rayon, or the like, or of natural fibers such as cotton. The non-woven material may also be substantially fluid-impermeable, so as to minimize an opportunity for fluid overflow from the absorbent insert 6 to pass therethrough. However, one of ordinary skill in the art may choose any other suitable material within the scope of the present disclosure.

With reference to FIGS. 1-2 and 4, each of the first and second patch 42a, 42b may have a first portion 48 and a second portion 50. The first portion 48 of the patch 42a, 42b may be adhered to the inner garment layer 8, the top layer 16 of the absorbent insert 6, the first leg cuff 32, and the second leg cuff 34. The second portion 50 is unadhered to the inner garment layer 8, the top layer 16 of the absorbent insert 6, the first leg cuff 32, and the second leg cuff 34, or otherwise free.

In particular embodiments, each of the first portions 48 of the first and second patches 42a, 42b may be adhered to the inner layer 8 of the garment layer 4 on three sides of the absorbent insert 6. Each of the first portions 48 of the first and second patches 42a, 42b, may also be adhered to the top layer 16 and each of the leg cuffs 32, 34 of the absorbent insert 6, as well as the garment layer 4. The first portions 48 of the first and second patches 42a, 42b may be adhered to the aforementioned layers through various adhesives 12, heat or ultrasonic bonding, or any by any other suitable means chosen by a skilled artisan.

For example, the first portion 48 of each of the first and second patches 42a, 42b where adhered on the three sides may be substantially U-shaped. The U-shaped first portion 48 may have a first arm section 52 and a second arm 54 section. The first arm 52 section may be spaced apart from the second arm section 54, and together define an area of the second portion 50 therebetween.

Additionally, as shown in FIGS. 1-2, the area defining the second portion 50 of patch 42a, 42b may be disposed entirely within the perimeter 30 of the base layer 20.

As described hereinabove, the second portion 50 of each of the first and second patches 42a, 42b is free from the top layer 16 of the absorbent insert 6. For example, there may be an absence of adhesive 12 between the top layer 16 of the absorbent insert 6 and the adjacent second portion 50 of each of the first and second patches 42a, 42b. Due to the absence of the adhesive 12, and as shown in FIG. 4, the free area between the second portion 50 of the patch 42a, 42b and the top layer 16 forms a pouch 56 for receiving the excess fluid in operation. The pouch 56 is defined by the first arm 52, the second arm 54, and the top layer 16 of the absorbent insert 6, and has an opening 57 that is configured to collect, redirect, and militate against excess fluid spilling out or away from the absorbent core 18.

With reference to FIG. 2, and in embodiments where there both the first patch 42a and the second patch 42b are employed at the opposite ends 26, 28 of the absorbent insert 6, the opening 57 of the first patch 42a may face the opening 57 of the second patch 42b. Advantageously, where the opening 57 of the first patch 42a faces the opening 57 of the second patch 42b, the disposable absorbent underwear product 2 may militate against excess fluid overflow from either the anterior or the posterior of the user in operation.

It should be appreciated that each of the first and second patches 42a, 42b may have a width W4 that is greater than the width W1 of the base layer 20 and the width W3 of the top layer 16. This difference in relative widths W1, W3, W4 advantageously allows the first and second ends 26, 28 of the absorbent insert 6 to be covered by the first and second patches 42a, 42b, respectively, on the three sides with the openings 57 facing each other. It should be appreciated the facing arrangement of the openings 57 may permit the product 2 to be worn by the user in either direction with the same effectiveness.

For example, with reference to FIGS. 3-4, each of the first and second patches 42a, 42b may have a length L3 and a width W4, and the second portion 50 of each of the first and second patches 42a, 42b, which defines the pouches 56, may have a length L4 and a width W5. The length L3 and the width W4 are selected so as to be able to cover an entirety of the first and second ends 26, 28 of the absorbent insert 6 with the first and second patches 42a, 42b, and the length L4 and the width W5 are selected so as to have pouches 56 sized to receive the first and second ends 22, 24 of the absorbent core 18 within the absorbent insert 6.

In one example, as shown in FIG. 3, the length L3 of each of the first and second patches 42a, 42b may be between eighty millimeters (80 mm) and one hundred and twenty millimeters (120 mm), and most particularly, may be one hundred millimeters (100 mm). The width W4 of each of the first and second patches 42a, 42b may be between about two hundred and twenty millimeters (220 mm) and about two hundred and eighty millimeters (280 mm), and most particularly, may be two hundred-and sixty millimeters (260 mm).

In a further example, as shown in FIG. 4, the length L4 of the second portion of each of the first and second patches 42a, 42b may be between about fifteen millimeters (15 mm) and about thirty-five millimeters (35 mm), and most particularly, may be about twenty-five mm (25 mm). The width W5 of the second portion 50 may be between about one hundred and twenty-five millimeter (125 mm) and about one hundred and sixty-five millimeter (165 mm), and most particularly, may be about one hundred and forty-five millimeter (145 mm).

It should be appreciated that the above-mentioned specific widths W4, W5 and lengths L3, L4 are being provided for illustration purposes only, with respect to a particular absorbent adult pant product 2 of the present disclosure, and are otherwise non-limiting. It should further be appreciated that one skilled in the art may select any other dimensions W4, W5, L3, L4 for the first and second patches 42a, 42b, and the second portions 50 of the first and second patches 42a, 42b, within the scope of the present disclosure.

As shown in FIGS. 6-8, and in addition to the first and second patches 42a, 42b, the disposable absorbent underwear product 2 further has first and second barriers 58a, 58b. Although described herein with respect to two barriers 58a, 58b, it should be appreciated that embodiments having a single barrier 58a, 58b are contemplated and considered within the scope of the present disclosure. The first and second patches 42a, 42b and the first and second barriers 58a, 58b advantageous operate together to militate against unwanted fluid overflow from the absorbent insert 6.

In certain embodiments, the first barrier 58a is disposed through the first patch 42a and the second barrier 58b is disposed through the second patch 42b. For example, each of the first and second patches 42a, 42b may be attached to the base layer 20 of the absorbent insert 6 and the garment layer 4 by the barrier 58a, 58b. It should be appreciated that each of the first and second barriers 58a, 58b therefore provides further structure for redirecting fluid flow back toward the absorbent insert 6 of the disposable absorbent underwear product 2 in operation.

As shown in FIGS. 6-8, each of the first and second barriers 58a, 58b may penetrate an associated one of the first and second patches 42a, 42b, as well as each of the leg cuffs 32, 34, the top layer 16, and at least a portion of the base layer 20 of the absorbent insert 6. It should be appreciated that the barrier 58a, 58b may not extend entirely through the base layer 20, but does serve to connect the first and second patches 42a, 42b to the base layer 20. Additionally, in certain embodiments (not shown) where the disposable absorbent underwear product 2 does not have the leg cuffs 32, 34, the first and second barriers 58a, 58b may alternatively penetrate just the associated one of first and second patch 42a, 42b, the top layer 16, and the portion of the base layer 20 of the absorbent insert 6.

With reference to FIG. 2, the first barrier 58a may be disposed between the first end 22 of the absorbent core 18 and the first terminal end 26 of the base layer 20. Likewise, the second barrier 58b may be disposed between the second end 24 of the absorbent core 18 and the second terminal end 28 of the base layer 20. This particular placement of the first barrier 58a and the second barrier 58b has been found to redirect the fluid flow to the absorbent core 6, and thereby militate against fluid overflow.

With reference to FIGS. 6-8, and as a non-limiting example, it should be appreciated that each of the first and second barriers 58a, 58b may be formed from a fluid-impermeable material such as a polymer that is disposed through and thoroughly intermingled with fibers or microstructure of the associated one of the first and second patches 42a, 42b, the top layer 16, the leg cuffs 32, 34, and the portion of the base layer 20. In this manner, the first and second barriers 58a, 58b cause the associated portions of the first and second patches 42a, 42b, the top layer 16, the leg cuffs 32, 34, and the base layer 20 with which they are intermingled to be resistant to fluid flow therethrough.

With reference to FIG. 4, the first and second barriers 58a, 58b may also have a length L5 that is equal to or greater than the width W1 of the base layer 20, but also less than the width W4 of the patch 42a, 42b. Where the first and second barriers 58a, 58b is longer than the width W1 of the base layer 20, it should be understood that a portion of the each of the first and second barriers 58a, 58b may be adhered to the garment layer 4 on either side of the base layer 20. In a further example, each of the first and second barriers 58a, 58b may a width W6 that minimizes an opportunity for fluid flow therethrough. It should also be appreciated that the length L5 and the width W6 of each of the first and second barriers 58a, 58b together militates against the overflow of fluids and redirects fluid back the absorbent core 18.

As shown in FIG. 6, the first and second barrier 58a, 58b may also extend substantially uninterrupted to the base layer 20, and as shown in FIG. 4, the first and second barrier 58a, 58b may also be disposed across an entirety of the base layer 20. Advantageously, it should be appreciated that the first and second barrier 58a, 58b being uninterrupted and disposed across the entirety of the base layer 20 creates a seal that militates against the undesired overflow of fluids past the base layer 20 to the garment layer 4.

In a particular non-limiting example, as shown in FIG. 4, the length L5 of each of the first and second barriers 58a, 58b may be between about two hundred and ten millimeters (210 mm) and about two hundred and fifty millimeters (250 mm), and most particularly, may be about two hundred and thirty millimeters (230 mm). The width W6 of each of the first and second barriers 58a, 58b may also be between one millimeter (1 mm) and five millimeters (5 mm), and most particularly, may be about three millimeters (3 mm).

It should be appreciated that the above-mentioned length L5 and width W6 of the first and second barriers 58a, 58b are being provided for illustration purposes only, with respect to a particular absorbent adult pant product 2 of the present disclosure, and are otherwise non-limiting. It should further be appreciated that one skilled in the art may select any other dimensions L5 and W6 for the first and second barriers 58a, 58b within the scope of the present disclosure.

As established hereinabove, the first and second barriers 58a, 58b are fluid-impermeable and preferably polymeric. For example, the first and second barriers 58a, 58b may be provided as an adhesive, a thermoplastic, or a thermoformable foam such as a polyethylene foam. However, one of ordinary skill in the art may select any other suitable fluid-impermeable material for the first and second barriers 58a, 58b, within the scope of the present disclosure.

In a most particular embodiment, the first and second barriers 58a, 58b may be an adhesive line made with normal hygiene construction hotmelt, or with an absorbent and water swellable-blocking hotmelt such as FULL-CARE® #9200 Hotmelt with the HYDROLOCK™ series of trade designations for useful hot melt superabsorbent polymer compositions, commercially available from H.B. Fuller Company in Vadnais Heights, Minn.

In operation, the first and second patches 42a, 42b and the first and second barriers 58a, 58b function synergistically to militate against excess moisture or fluid escaping from the absorbent insert 6 or otherwise leaking into the surrounding garment layer 4. As established hereinabove, the second portion 50 of each of the first and second patches 42a, 42b forms the pouches 56 of the disposable absorbent underwear product 2. A rear of each of the pouches 56 is spaced apart from but disposed adjacent to an associated one of the first and second barriers 58, as shown in FIG. 4.

The openings 57 of the pouches 56 function to initially receive and capture the excess fluid and to redirect the excess fluid back toward the absorbent core 18, while the barrier 58a, 58b militates against fluid leaking beyond the base layer 20 of the absorbent insert 6. Furthermore, the use of hydrophobic non-woven material for the first and second patches 42a, 42b has been found advantageous for this purpose, since such hydrophobic material does not readily absorb liquids. Consequently, the moisture or liquid is redirected back toward the absorbent core 18 and is not absorbed by the first and second patches 42a, 42b. The first and second barriers 58a, 58b also form seals between the hydrophobic materials of the first and second pages 42a, 42b and the base layer 20, thereby directing substantially all captured fluid back to the absorbent core 18.

It should be appreciated that the disposable absorbent underwear product 2 described hereinabove may be manufactured using otherwise conventional absorbent inserts 6 and garment layers 4, with the first and second patches 42a, 42b and the first and second barriers 58a, 58b being added during the manufacturing process. Alternatively, the use of a pre-assembled absorbent insert 6 having the first and second patches 42a, 42b and the first and second barriers 58a, 58b assembled with the absorbent insert 6 prior to placement in the garment layer 4 is also contemplated, and considered to be within the scope of the present disclosure.

Advantageously, the disposable absorbent underwear product 2 described hereinabove, containing the first and second patches 42a, 42b together with the fluid-impermeable barriers 58, 58b, militates against the overflow of excess fluid to the garment layer 8 by redirecting the fluid to the absorbent core 18 of the product 2 in operation.

While certain representative embodiments and details have been shown for purposes of illustrating the invention, it will be apparent to those skilled in the art that various changes may be made without departing from the scope of the disclosure, which is further described in the following appended claims.

What is claimed is:

1. A disposable absorbent underwear product, comprising:
a garment layer;
an absorbent insert disposed on the garment layer, the absorbent insert having a top layer that is fluid-permeable, an absorbent core, and a base layer that is fluid-impermeable, the absorbent core having a first end and a second end, and the base layer having a first terminal end and a second terminal end, the first end of the absorbent core being spaced apart from the first terminal end of the base layer;

a non-woven patch disposed on and covering the first terminal end of the base layer of the absorbent insert, the non-woven patch having a first portion and a second portion, the first portion of the non-woven patch adhered to both the top layer of the absorbent insert and the garment layer, the second portion of the non-woven patch being bounded by the first portion and being unadhered to the top layer of the absorbent insert, and the second portion of the non-woven patch together with the top layer of the absorbent insert defining a pouch with an opening;

a barrier disposed through each of the first portion of the non-woven patch and the top layer of the absorbent insert and connected to the base layer of the absorbent insert, the barrier also disposed between the first end of the absorbent core and the first terminal end of the base layer of the absorbent insert and configured to direct fluid flow to the absorbent core and militate against fluid overflow; and a pair of leg cuffs including a first leg cuff and a second leg cuff, the first leg cuff and the second leg cuff each disposed on opposing sides of the absorbent core and between the top layer of the absorbent insert and the non-woven patch.

2. The disposable absorbent underwear product of claim 1, wherein the base layer has a perimeter, and an entirety of the second portion of the non-woven patch is disposed within the perimeter of the base layer.

3. The disposable absorbent underwear product of claim 1, wherein the patch is adhered to the garment layer adjacent three sides of the absorbent insert.

4. The disposable absorbent underwear product of claim 1, wherein the first portion of the non-woven patch is adhered to each of the garment layer, the top layer, the first leg cuff, and the second leg cuff.

5. The disposable absorbent underwear product of claim 4, wherein the barrier is also disposed through the first leg cuff and the second leg cuff of the absorbent insert.

6. The disposable absorbent underwear product of claim 1, wherein the first portion of the non-woven patch is substantially U-shaped and has a pair of arm sections, and the pouch is disposed between the arm sections.

7. The disposable absorbent underwear product of claim 1, wherein the barrier is formed from a thermoformable foam or a construction hotmelt.

8. The disposable absorbent underwear product of claim 1, wherein the non-woven patch is formed from a substantially fluid-impermeable non-woven material.

9. The disposable absorbent underwear product of claim 1, wherein the non-woven patch is a first non-woven patch, and the disposable absorbent underwear product further includes a second non-woven patch, the second non-woven patch disposed on and covering the second terminal end of the base layer of the absorbent insert, the second non-woven patch having a first portion and a second portion, the first portion of the second non-woven patch adhered to both the top layer of the absorbent insert and the garment layer, the second portion of the second non-woven patch being bounded by the first portion and together with the top layer of the absorbent insert defining a pouch with an opening.

10. The disposable absorbent underwear product of claim 9, wherein the opening of the pouch of the second non-woven patch faces the opening of the pouch of the first non-woven patch.

11. The disposable absorbent underwear product of claim 9, wherein the barrier layer is a first barrier layer, and the disposable absorbent underwear product further includes a second barrier disposed through each of the first portion of the second non-woven patch and the top layer of the absorbent insert and connected to the base layer of the absorbent insert, the second barrier also disposed between the second end of the absorbent core and the second terminal end of the base layer of the absorbent insert and configured to direct fluid flow to the absorbent core and militate against fluid overflow.

12. A disposable absorbent underwear product, comprising:

a garment layer;

an absorbent insert disposed on the garment layer, the absorbent insert having a top layer that is fluid-permeable, an absorbent core, and a base layer that is fluid-impermeable, the base layer having a base layer width;

a non-woven patch disposed on and covering the top layer of the absorbent insert, the non-woven patch having a first portion and a second portion, the first portion of the non-woven patch adhered to the top layer of the absorbent insert and the garment layer, the first portion of the non-woven patch being substantially U-shaped with a pair of arm sections, the second portion of the non-woven patch disposed between the arm sections, the second portion of the non-woven patch being bounded by the first portion and together with the top layer of the absorbent insert defining an open pouch; and a barrier disposed through each of the first portion of the non-woven patch and the top layer of the absorbent insert and connected to the base layer of the absorbent insert, the barrier having a barrier length, wherein the barrier length is greater than the base layer width, and the barrier is adhered to the garment layer on opposing sides of the base layer, wherein the barrier is disposed across an entirety of the base layer width, and wherein the non-woven patch has a patch width, and the barrier length is less than the patch width.

13. A disposable absorbent underwear product, comprising:

a garment layer;

an absorbent insert disposed on the garment layer, the absorbent insert having a top layer that is fluid-permeable, an absorbent core, and a base layer that is fluid-impermeable, the absorbent core having a first end and a second end, and the base layer having a first terminal end and a second terminal end, the first end of the absorbent core being spaced apart from the first terminal end of the base layer;

a first non-woven patch disposed on and covering the first terminal end of the base layer of the absorbent insert, the first non-woven patch having a first portion and a second portion, the first portion of the first non-woven patch adhered to both the top layer of the absorbent insert and the garment layer, the second portion of the first non-woven patch being bounded by the first portion and being unadhered to the top layer of the absorbent insert, and the second portion of the first non-woven patch together with the top layer of the absorbent insert defining a first pouch with a first opening;

a first barrier disposed through each of the first portion of the first non-woven patch and the top layer of the absorbent insert and connected to the base layer of the absorbent insert, the first barrier also disposed between the first end of the absorbent core and the first terminal end of the base layer of the absorbent insert and configured to direct fluid flow to the absorbent core and militate against fluid overflow;

a second non-woven patch, the second non-woven patch disposed on and covering the second terminal end of the base layer of the absorbent insert, the second non-woven patch having a first portion and a second portion, the first portion of the second non-woven patch adhered to both the top layer of the absorbent insert and the garment layer, the second portion of the second non-woven patch being bounded by the first portion and together with the top layer of the absorbent insert defining a second pouch with a second opening;

a second barrier disposed through each of the first portion of the second non-woven patch and the top layer of the absorbent insert and connected to the base layer of the absorbent insert, the second barrier also disposed between the second end of the absorbent core and the second terminal end of the base layer of the absorbent insert and configured to direct fluid flow to the absorbent core and militate against fluid overflow, the second opening of the second pouch of the second non-woven patch faces the first opening of the first pouch of the first non-woven patch; and a pair of leg cuffs including a first leg cuff and a second leg cuff, the first leg cuff and the second leg cuff each disposed on opposing sides of the absorbent core and between the top layer of the absorbent insert and the first non-woven patch.

14. A disposable absorbent underwear product, comprising:

a garment layer;

an absorbent insert disposed on the garment layer, the absorbent insert having a top layer that is fluid-permeable, an absorbent core, and a base layer that is fluid-impermeable, the absorbent core having a first end and a second end, and the base layer having a first terminal end and a second terminal end, the first end of the absorbent core being spaced apart from the first terminal end of the base layer;

a non-woven patch disposed on and covering the first terminal end of the base layer of the absorbent insert, the non-woven patch having a first portion and a second portion, the first portion of the non-woven patch adhered to both the top layer of the absorbent insert and the garment layer, the second portion of the non-woven patch being bounded by the first portion and being unadhered to the top layer of the absorbent insert, and the second portion of the non-woven patch together with the top layer of the absorbent insert defining a pouch with an opening; and a barrier disposed through each of the first portion of the non-woven patch and the top layer of the absorbent insert and connected to the base layer of the absorbent insert, the barrier also disposed between the first end of the absorbent core and the first terminal end of the base layer of the absorbent insert and configured to direct fluid flow to the absorbent core and militate against fluid overflow, wherein the base layer of the absorbent insert has a base layer width, and the barrier has a barrier length, and the barrier length is equal to or greater than the base layer width, the barrier length is greater than the base layer width, and the barrier is adhered to the garment layer on opposing sides of the base layer.

15. The disposable absorbent underwear product of claim 14, wherein the barrier is disposed across an entirety of the base layer width.

16. The disposable underwear product of claim 14, wherein the non-woven patch has a patch width, and the barrier length is less than the patch width.

* * * * *